United States Patent [19]

Kontani et al.

[11] Patent Number: 4,719,360

[45] Date of Patent: Jan. 12, 1988

[54] METHOD FOR DETERMINATION OF CONCENTRATION OF SMOKE EMANATING FROM COMBUSTION ENGINE AND APPARATUS FOR WORKING SAID METHOD

[75] Inventors: Kazuo Kontani; Shinichi Goto, both of Ibaraki, Japan

[73] Assignees: Agency of Industrial Science & Technology; Ministry of International Trade & Industry, both of Tokyo, Japan

[21] Appl. No.: 838,585

[22] Filed: Mar. 11, 1986

[30] Foreign Application Priority Data

Mar. 11, 1985 [JP] Japan .................................. 60-47980
Aug. 26, 1985 [JP] Japan ................................. 60-186819

[51] Int. Cl.4 ............................................. G01N 15/06
[52] U.S. Cl. .................................... 250/574; 250/575; 356/438
[58] Field of Search .................... 250/573, 574, 575; 356/338, 339, 335, 336, 342, 343, 436, 437, 438, 439

[56] References Cited

U.S. PATENT DOCUMENTS

| | | | |
|---|---|---|---|
| 3,700,330 | 10/1972 | Davis | 356/335 |
| 3,994,603 | 11/1976 | Paschedag | 356/438 |
| 4,168,438 | 9/1979 | Morisue | 356/438 |
| 4,265,535 | 5/1981 | Pitt | 250/574 |
| 4,386,854 | 6/1983 | Byer | 356/438 |
| 4,420,256 | 12/1983 | Fladda et al. | 356/336 |
| 4,449,816 | 5/1984 | Kohsaka et al. | 356/336 |
| 4,473,296 | 9/1984 | Shofner et al. | 356/338 |

Primary Examiner—David C. Nelms
Assistant Examiner—William L. Oen
Attorney, Agent, or Firm—Oblon, Fisher, Spivak, McClelland, & Maier

[57] ABSTRACT

Concentration of a smoke emanating from a combustion engine is determined by projecting beams of light on the flow of smoke in directions traversing the flow of smoke, detecting intensities of beams of light which have traversed the flow of smoke with a light receiving device and calculating a cross-sectional image of the flow of smoke based on detection signals issued by the light receiving device.

4 Claims, 7 Drawing Figures

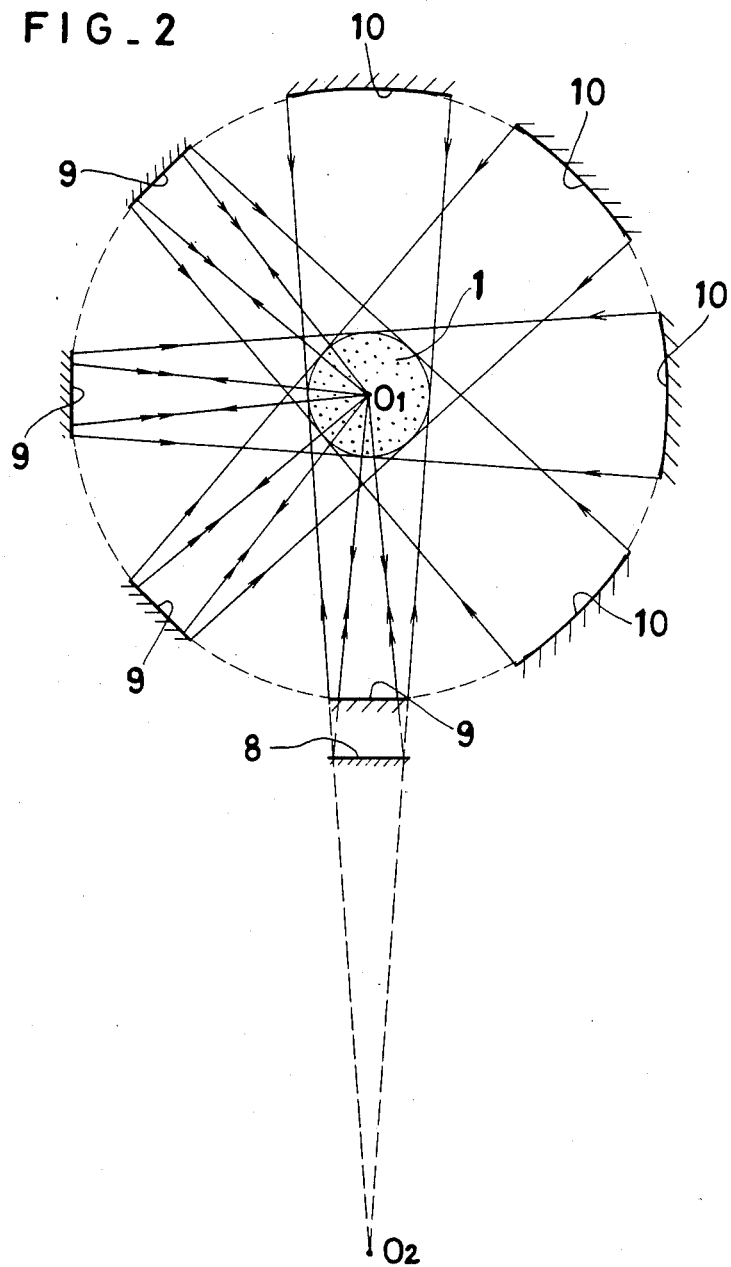
FIG_2

FIG_3
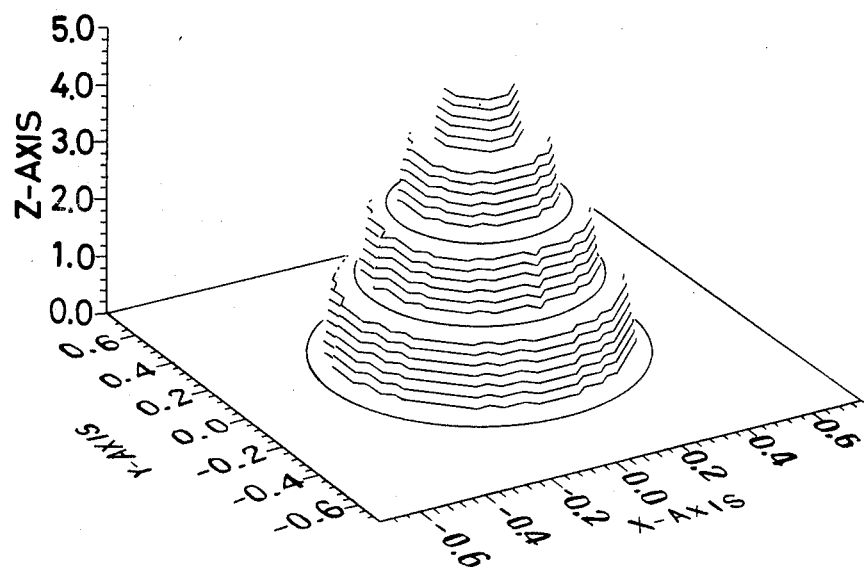

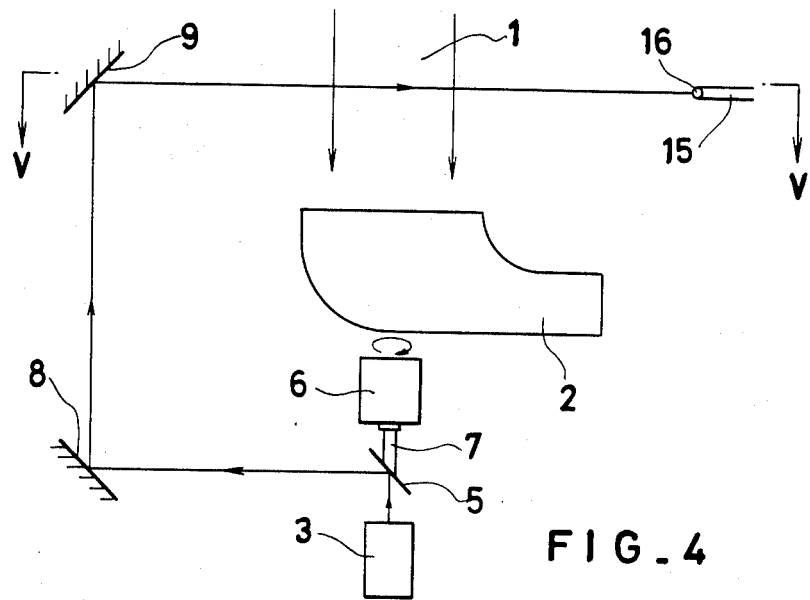
FIG._4
FIG._5
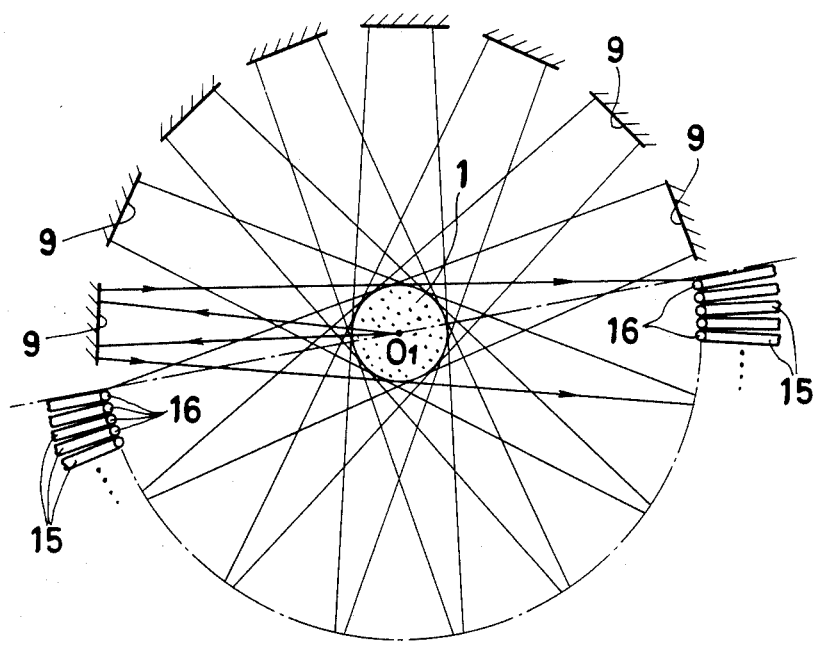

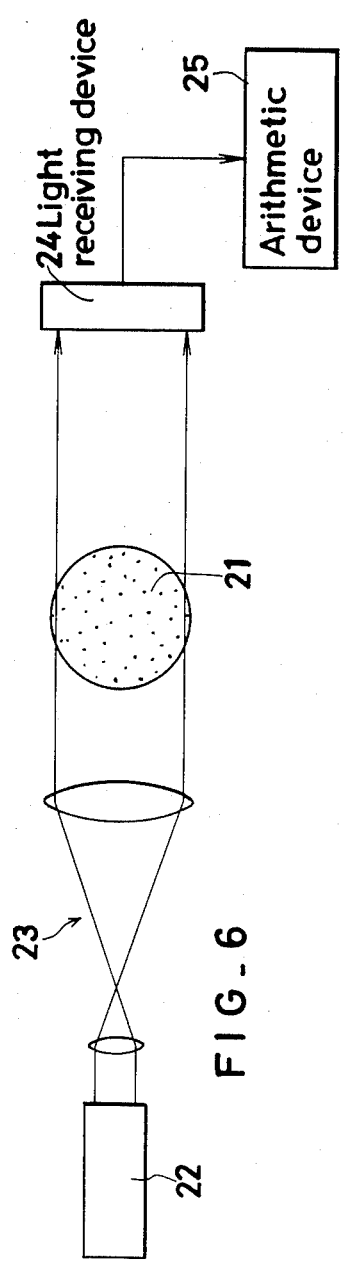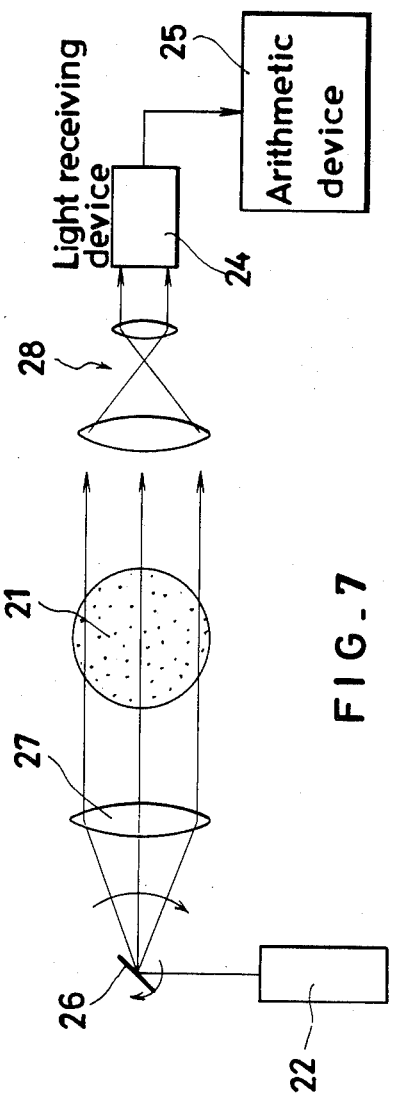
FIG.-6
FIG.-7

METHOD FOR DETERMINATION OF CONCENTRATION OF SMOKE EMANATING FROM COMBUSTION ENGINE AND APPARATUS FOR WORKING SAID METHOD

BACKGROUND OF THE INVENTION

1. Field of the Invention

This invention relates to a method for the determination of the absolute values of volume concentration and weight concentration of fine carbon particles in a flow of smoke emanating from a combustion engine and to an apparatus for working the method.

2. Discussion of Background

Heretofore, as means of determining concentration of smoke emanating as from a combusion engine, the method which has recourse to a Bosch smokemeter and the method which is specified in a U.S. glossary of testing methods have prevailed. The former method determines the concentration of smoke by causing fine carbon particles in the smoke to be suction deposited on a filter paper and measuring the reflectance of light on the filter paper and the latter method determines the concentration of smoke by allowing the smoke to flow spontaneously in its own course, throwing a white light sidewise upon the smoke, and measuring the opacity (degree of imperviousness) of the smoke relative to the light impinging thereon.

The methods of determination mentioned above rely for measurement of specific physical magnitudes upon their own arbitrary scales and consist in performing relevant measurements in accordance with respectively prescribed rules. Thus, the values of measurement obtained by these different methods vary in significance. In the existing circumstance, it is difficult to seek and fix any absolute relation among these different methods of determination. In other words, by any of the methods described above, it is difficult to know the absolute concentration of fine carbon particles in the flow smoke emanating from a combustion engine.

OBJECT AND SUMMARY OF THE INVENTION

An object of this invention is to provide a method and apparatus for determining easily and accurately the absolute values of volume concentration and weight concentration of fine carbon particles in a flow of smoke emanating from a combustion engine.

Another object of this invention is to provide a method and apparatus for determining continuously on the real-time basis the absolute values of volume concentration and weight concentration of fine carbon particles in a flow of smoke emanating from a combustion engine.

To be specific, this invention determines the absolute values of volume concentration and weight concentration of fine carbon particles in a flow of smoke emanating from a combustion engine by projecting transversely on the flow of smoke the light of a wavelength capable of causing Rayleigh scattering relative to the fine carbon particles, detecting the portion of the light which has traversed the flow of smoke, and producing a cross-sectional image of the flow of smoke based on the calculation using the resulting detection signal.

In the present invention, since the light of a single wavelength to be projected on the flow of smoke is defined as a light possessing a relatively long wavelength capable of causing Rayleigh scattering relative to the fine carbon particles, the absorption and scattering of the light of the single wavelength caused by the fine carbon particles is obtained as variations of transmittance of the light accurately corresponding to the volume concentration of the fine carbon particles. By detecting variations of intensity of the light which has traversed the flow of smoke and producing a cross-sectional image of the flow of smoke from the results of the detection with the aid of an electronic computer, therefore, the absolute values of volume concentration and weight concentration of the fine carbon particles in the flow of smoke can be determined continuously on the real-time basis.

The other objects and characteristics of the present invention will become apparent from the description given in further detail hereinbelow with reference to the accompanying drawings.

BRIEF DESCRIPTION OF THE DRAWINGS

FIG. 2 is a cross sectional view taken along the line II—II of FIG. 1.

FIG. 3 is a simulated cross-sectional image of the concentration of carbon particles in the flow of smoke obtained in accordance with the present invention.

FIG. 4 is a schematic explanatory view illustrating another apparatus for effecting determination of smoke concentration by the method of this invention.

FIG. 5 is a cross sectional view taken along the line V—V of FIG. 4.

FIG. 6 is a schematic explanatory view illustrating still another apparatus for effecting determination of smoke concentration by the method of this invention.

FIG. 7 is a schematic explanatory view of an apparatus as a partially modified version of the apparatus of FIG. 6.

DESCRIPTION OF PREFERRED EMBODIMENTS

Figure 1:
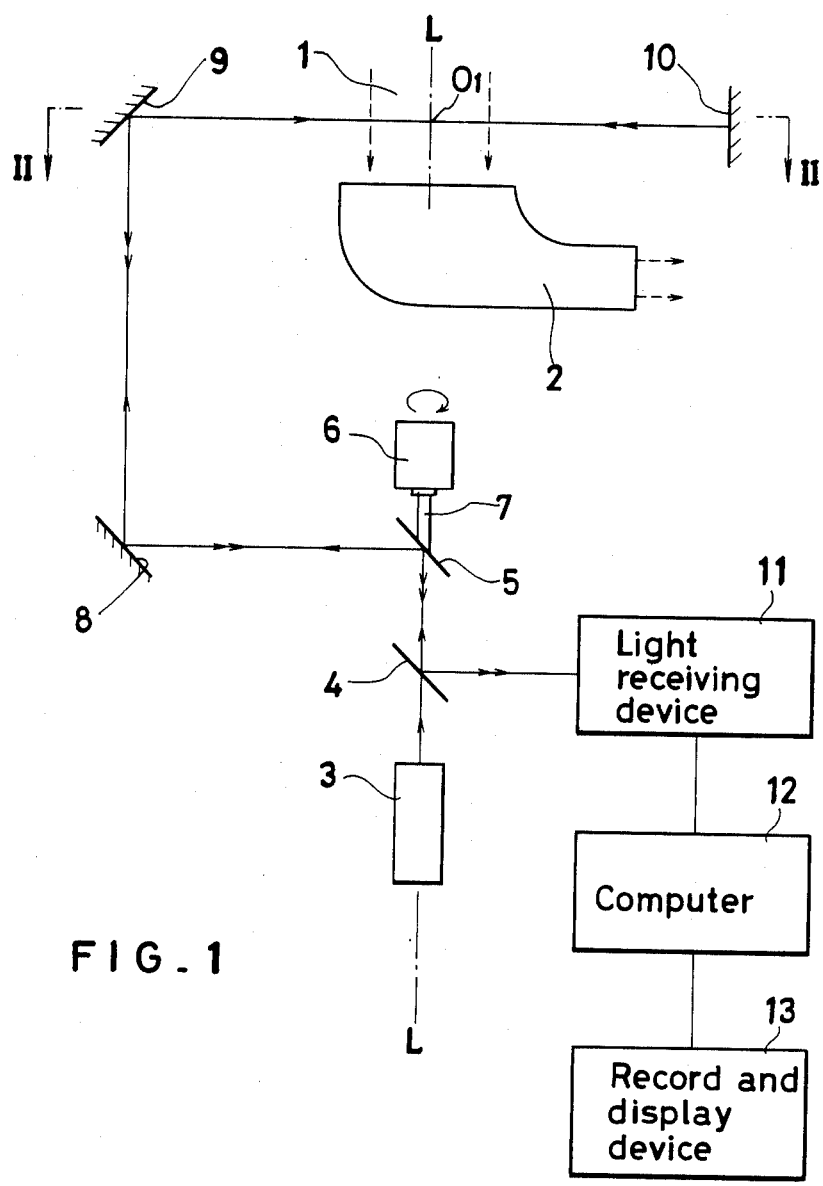
FIG. 1 is a schematic explanatory view illustrating a typical apparatus for effecting determination of smoke concentration by the method of the present invention.

First, the principle of this invention will be described.

Generally, the smoke emanating from a combustion engine has fine carbon particles distributed in a highly irregular state therein. When a light is transversely passed through the flow of smoke, the distribution of attenuation of the penetrating light varies depending on the direction in which the light is passed. By causing the light to traverse the flow of smoke in as many directions as permissible, measuring the state of attenuation of the light in all such directions, and producing by calculation a cross-sectional image of the flow of smoke based on the results of measurement, therefore, the volume concentration and weight concentration of fine carbon particles in the flow of smoke can be accurately found.

The first embodiment of this invention for the determination of smoke concentration is based on the principle described above. With reference to FIG. 1, 1 denotes a flow of smoke emanating from a combustion engine. It is allowed to flow in the air in the form of a free stream about 5 cm in diameter. A duct 2 for receiving the flow of smoke 1 is disposed downstream relative to the course of the flow of smoke.

A light of a single wavelength is projected on the flow of smoke 1 in a plurality of directions traversing the flow of smoke and a cross-sectional image of the flow of smoke is produced by a calculation using the intensities of the beams of light which have traversed the flow of smoke. In an apparatus required for this operation, a He-Ne gas laser, for example, is disposed as a light source 3 on the same axis as an axial line L of the flow of smoke 1. The laser beam emitted from the light source 3 has a wavelength capable of producing Rayleigh scattering such that the absorption and scattering of the laser beam by the fine carbon particles will be obtained in the form of variations of transmittance of light corresponding to the volume concentration of weight concentration of the fine carbon particles. Specifically a light having a wavelength of not less than about 0.6 μm answers this description. Particularly, a beam of a wavelength of 0.6328 μm or 1.15 μm emitted from a He-Ne gas laser can be used advantageously.

In front of the laser beam source 3 is disposed an inclined rotary mirror 5 adapted to reflect the laser beam through the medium of a half mirror 4. The rotary mirror 5 is fixed diagonally to a rotary shaft 7 of a motor 6 disposed on the same axis as the axial line L mentioned above. In this arrangement, as the rotary mirror 5 is rotated jointly with the rotary shaft 7, the direction in which the laser beam reflected by the rotary mirror 5 advances is caused to revolve around the axial line L.

Further, as illustrated in FIG. 1 and FIG. 2, a plurality of plane mirrors 8 are disposed around the rotary mirror 5 and stationary plane mirrors 9 are disposed around the zone of measurement of the flow of smoke 1 and on the optical axes of the plane mirrors 8 and as many stationary concave mirrors 10 as the plane mirrors 9 are disposed as opposed to the stationary plane mirrors 9 across the flow of smoke 1 so that the reflected beam from the rotary mirror 5 may be turned in directions traversing the flow of smoke 1. In the illustrated embodiment, the plurality of plane mirrors 9 are disposed in one half of the circumference of a circle drawn around the center $O_1$ of the flow of smoke 1 and the concave mirrors 10 are disposed in the remaining half of the circumference at the positions opposed to those of the plane mirrors 9 across the flow of smoke. The stationary plane mirrors 8, 9 and the stationary concave mirrors 10 are disposed in such a manner that, as apparent from FIG. 2, the beams reflected by these mirrors will traverse the flow of smoke 1 while scanning the entire cross section of the flow of smoke and, at the same time, advance along the same optical paths and impinge again upon the rotary mirror 5. The centers $O_2$ of curvature of the concave mirrors 10 fall on the line produced by extending the lines of distance from the rotary mirror 5 to the plane mirrors 9 in the directions opposite those from the mirrors 8 toward the concave mirrors 10.

As a result, the laser beam reflected by the rotary mirror 5 is reflected by the plane mirrors 8, 9, then passed through the flow of smoke 1, allowed to impinge on the concave mirror 10, subsequently advanced backwardly through the same optical paths, and caused to impinge on the rotary mirror 5. Thus, the laser beam traverses the flow of smoke 1 forward and backward and, during each of the traverses, undergoes reflection and scattering in the form of Rayleigh scattering on impinging upon the fine carbon particles.

As shown in FIG. 2, a plurality of sets of plane mirrors 8, 9 and concave mirrors 10 are disposed around the region of measurement encompassing the flow of smoke 1.

The laser beams which have been reciprocated between the plane mirrors 8, 9 and the concave mirrors 10 and returned to the rotary mirror 5 are again reflected by the rotary mirror 5 and caused to impinge upon the half mirror 4. The laser beams which have been reflected by the half mirror 5 are projected on a light receiving device 11 for detection of variations in intensity of the laser beam. The reflected beams emitted from the plane mirrors 9 and the concave mirrors 10 at successive positions assumed by the rotary mirror 5 during its rotation are sequentially projected into the light receiving device 11.

The light receiving device 11 is connected with the computer 12 for processing signals of detection obtained at the light receiving device 11 and a recording and displaying device 13 for recording and displaying the results of processing. The computer 12 is for calculating the signals of detection from the light receiving device 11 and produce a cross-sectional image of the flow of smoke based on the results of the calculation.

The apparatus constructed as described above effects the determination of the volume concentration of fine carbon particles in the flow of smoke 1, as inferred from the description given so far, by rotating the rotary mirror 5 relative to the flow of smoke 1 in the form of a free stream and causing the laser beam to be successively projected on the plane mirrors 8 disposed around the rotary mirror 5 and, whenever the laser beams impinge upon the plane mirrors 9 through the medium of the plane mirrors 8, causing the plane mirrors 9 to cooperate with the stationary concave mirrors 10 opposed thereto, thereby allowing the laser beams to traverse the flow of smoke throughout the entire cross section of the flow of smoke 1, and enabling the light receiving device 11 to receive the laser beams which have traversed the flow of smoke and effect detection of variations of intensity of the laser beams. This operation is repeated each time that plane mirrors 8, 9 receiving the impinging laser beams are shifted to the adjoining plane mirrors 8, 9 in consequence of the rotation of the rotary mirror 5. By this repetition of the operation, the flow of smoke 1 is irradiated with the laser beams advancing in successively shifted directions of radiation, to permit detection of variations of intensity. As the computer 12 calculates the resulting values of detection and produces a cross-sectional image of the flow of smoke, the absolute values of volume concentration and weight concentration of the fine carbon particles in the flow of smoke are obtained and recorded and displayed by the recording and displaying device 13.

FIG. 3 represents a simulated cross-sectional image of the concentration of fine carbon particles in the flow of smoke obtained by the computer. It depicts a typical calculation assuming a state in which the concentration of fine carbon particles is larger at the center of the cross section of the flow of smoke, to verify algorithm of the CT calculation used.

The speed of rotation of the rotary mirror during the measurement described above is desired to be as high as possible because it affects the resolvability of the flow of smoke in the direction of its movement. The present invention fixes the maximum speed of rotation at 3000 rpm in due consideration of the mechanical conditions, the accuracy of the algorithm of data calculation, etc. This speed of rotation is such that the resolvability (interval of resolution) in the direction of flow is about 20 mm when the flow speed of the flow of smoke is 2 m/sec. Thus, the concentration of fine carbon particles in the flow of smoke can be determined substantially completely.

Determination of the concentration of smoke can otherwise be effected by the use of an apparatus which is constructed as illustrated in FIG. 4 and FIG. 5.

This apparatus has light receiving ends 16 of a multiplicity of optical fibers 15 arrayed at the positions corresponding to those occupied by the concave mirrors 10 of the apparatus of FIGS. 1 and 2 so as to serve as substitutes for the concave mirrors 10. These optical fibers 15 have their other ends connected to a single light receiving device (not shown). Further, this light receiving device is connected to a computer and a recording and displaying device similarly to that in the device of the preceding embodiment, to enable the calculation of a cross-sectional image and the consequent determination of volume concentration and weight concentration of fine carbon particles in the flow of smoke to be effected substantially similarly to those obtained by the apparatus of FIG. 1.

In the apparatus just described, the laser beams are not reciprocated through the flow of smoke 1 but passed just once therethrough and the laser beams which have traversed the flow of smoke 1 are forwarded through the optical fibers 15 and received by the light receiving device. In the light receiving device, the intensities of light received by the optical fibers are sequentially varied enough to tell which optical fibers have detected traversing beams at their light receiving ends. At the same time, through comparison of the values of measurement obtained by the light receiving device with the values of correction produced in the absence of the flow of smoke in the region of measurement, the degrees of decrease of light by the flow of smoke can be detected. Based on the results of measurement, therefore, the calculation of a cross-sectional image is effected and, at the same time, the determination of both volume concentration and weight concentration of fine carbon particles in the flow of smoke is attained.

The first embodiment described above effects the determination of concentration of fine carbon particles by projecting beams of light upon the flow of smoke in a plurality of directions traversing the flow of smoke because the fine carbon particles are distributed in an extremely uneven manner in the flow of smoke. Assuming that the fine carbon particles in the flow of smoke are evenly distributed around the central axial line of the flow of smoke, it can be concluded that the beams of light traversing the flow of smoke in various directions are attenuated in one fixed manner. It is logically inferred that the concentration of fine carbon particles in the flow of smoke can be determined by projecting the beam of light on the flow of smoke in one direction and calculating a cross-sectional image of the flow of smoke from the magnitude of attenuation of the traversing beam of light.

Now, the determination of smoke concentration based on the principle described above will be explained below as the second embodiment of this invention with reference to FIGS. 6 and 7. Now, referring to FIG. 6, 21 denotes a flow of smoke emanating from a combustion engine as depicted in a cross section perpendicularly intersecting the direction of the flow of smoke. The flow of smoke is released into the ambient air in the form of a free stream about 5 cm in diameter. It is discharged through a duct (not shown) disposed downstream relative to the direction of the flow of smoke.

On one side of the flow of smoke is disposed a light source 22 for projecting a laser beam, for example. As the light to be projected by the light source 22, there is used a laser beam which, similarly to the light used in the first embodiment, has a relatively long wavelength and enables the absorption and scattering of light by the fine carbon particles to be handled as Rayleigh scattering. White light, for example, may be used where the spectral properties inclusive of the light source and the light receiving device are known in advance.

In front of the light source is disposed a collimator 23. A light receiving device 24 for detecting the intensity of the light which has traversed a flow of smoke 21 is opposed to the collimator 23 across the flow of smoke 21. In this arrangement, the beam of light which has traversed the flow of smoke 21 in one direction is detected by the light receiving device 24. The light receiving device 24 used herein is an array type detector having a multiplicity of light detecting elements arranged in an array. An arithmetic device 25 is connected to the light receiving device 24. The arithmetic device 25 is composed of a computer and is possessed of a function of calculating a fictitious cross-sectional image of the flow of smoke 21 based on the output of the light receiving device 24 and calculating the absolute values of volume concentration and weight concentration of fine carbon particles in the flow of smoke 21 on the assumption that the fine carbon particles are evenly distributed coaxially in the flow of smoke 21, i.e. the assumption that when the light traverses the flow of smoke, the condition of attenuation of light is equal no matter in which direction the traverse may be made.

In the apparatus constructed as described above, when the light from the light source 22 is projected on the flow of smoke 21 emanating from a diesel engine, for example, this light traverses the flow of smoke 21 from one side of the other. During this traverse, the light is attenuated by the fine carbon particles. The light, in the form so attenuated, impinges upon the light detection elements of the light receiving device 24. The individual light detection elements in the light receiving device 24 issue detection signals in the form of parallel data corresponding to the state of distribution of the fine carbon particles in the flow of smoke 21 and pass these detection signals into the arithmetic device 25. Consequently, in the arithmetic device 25, the absolute values of volume concentration and weight concentration of the fine carbon particles in the flow of smoke are calculated.

FIG. 7 illustrates another embodiment resulting from partial modification of the embodiment illustrated in FIG. 6. It differs from the first embodiment of FIG. 6 in respect that the laser beam from the light source is caused to scan the flow of smoke, namely the laser beam is translated in the direction of the diameter of the flow of smoke and is allowed to traverse the flow of smoke and, at the same time, the conditions of attenuation of the traversing beam of light is sequentially detected by the light receiving device formed of single light detecting elements.

Referring to FIG. 7, 26 denotes a rotary mirror for revolving the laser beam projected from the laser beam source 22 for the purpose of scanning, 27 a lens system for causing the laser beams from the rotary mirror 26 to be directed translationally toward the flow of smoke 21, 28 a lens system for causing the laser beams which have traversed the flow of smoke 21 to impinge upon the light receiving device 24, and 25 an arithmetic device similar to the arithmetic device illustrated in FIG. 6.

In the apparatus constructed as described above, when the mirror 26 is rotated in the direction of the arrow, for example, the laser beams as held in the form of spotlights are translated downwardly in the bearing of FIG. 7 and are allowed to traverse the flow of smoke 21. As the result, the flow of smoke 21 is scanned by the laser beams in the direction of the diameter. The laser beams which have traversed the flow of smoke are caused by the lens system 27 to impinge upon the light receiving device 26, with the result that data produced sequentially are forwarded in the order of occurrence to the arithmetic device.

A light receiving device having a multiplicity of light detection elements arranged in an array similarly to the light receiving device (optical fiber) of FIG. 5 may be used in the place of the lens system 28 and the light receiving device 24. In this case, whenever the beams of light which have traversed the flow of smoke are translated, they sequentially impinge upon the light detecting elements arranged in an array and the outputs of the individual detection elements are sequentially transmitted to the arithmetic device. In the arithmetic device, substantially similar to that of FIG. 1, a fictitious cross-sectional image of the flow of smoke is calculated and the absolute values of volume concentration and weight concentration of fine carbon particles in the flow of smoke are calculated.

This invention need not be limited to the embodiments described above. An apparatus for working this invention may be formed of a plurality of sets of laser beam sources and light receiving devices, which are arranged in such a manner that a plurality of laser beams from the laser beam sources are simultaneously projected on the flow of smoke and the laser beams which have traversed the flow of smoke are received by the corresponding light receiving devices. As the result, the determination of of volume concentration and weight concentration of the fine carbon particles can be effected with high speed of response.

What is claimed is:

1. A method for the determination of concentration of smoke emanating from a combustion engine, which comprises projecting, into a flow of smoke in a plurality of directions traversing said flow of smoke, beams of light having a single wavelength capable of causing Rayleigh scattering relative to said fine carbon particles contained in said flow of smoke, detecting intensities of beams of light from the plurality of directions with a light receiving device, which beams of light have traversed said flow of smoke and attenuated due to the Rayleigh scattering, and determining absolute values of volume concentration and weight concentration of the fine carbon particles in said flow of smoke by calculating a cross-sectional image of said flow of smoke based on detection signals issued by said light receiving device.

2. A method according to claim 1 wherein beams of light are projected in directions traversing the whole cross-sectional area of the flow of smoke.

3. An apparatus for the determination of concentration of a smoke emanating from a combustion engine, which comprises a light source for projecting beams of light having a single wavelength capable of causing Rayleigh scattering relative to fine carbon particles so as to traverse a flow of smoke from said combustion engine, a light receiving device for subsequently detecting intensities of the beams of light which have traversed said flow of smoke, and an arithmetic device for calculating absolute values of volume and weight concentrations of said fine carbon particles in said flow of smoke based on detection signals issued by said light receiving device.

4. An apparatus according to claim 3, wherein beams of light which have traversed are received by a plurality of optical fibers and led to light receiving devices connected to leading ends of said optical fibers.

* * * * *